(12) United States Patent
Sharrock

(10) Patent No.: US 7,879,624 B2
(45) Date of Patent: Feb. 1, 2011

(54) ASSAY DEVICE WITH SHARED ZONES

(75) Inventor: Stephen Paul Sharrock, Bedford (GB)

(73) Assignee: Alere Switzerland GmbH, Zug (CH)

( * ) Notice: Subject to any disclaimer, the term of this patent is extended or adjusted under 35 U.S.C. 154(b) by 250 days.

(21) Appl. No.: 12/199,284

(22) Filed: Aug. 27, 2008

(65) Prior Publication Data

US 2009/0061534 A1    Mar. 5, 2009

Related U.S. Application Data

(60) Provisional application No. 60/991,543, filed on Nov. 30, 2007.

(30) Foreign Application Priority Data

Sep. 1, 2007   (GB) .................................. 0717045.9
May 31, 2008   (GB) .................................. 0809994.7

(51) Int. Cl.
   *G01N 33/53*   (2006.01)
(52) U.S. Cl. ...................... 436/518; 436/514; 436/805; 435/287.1; 435/287.2; 435/287.7; 435/808
(58) Field of Classification Search ................ 436/514, 436/518, 805; 435/287.1, 287.2, 287.7, 808
   See application file for complete search history.

(56) References Cited

U.S. PATENT DOCUMENTS

| | | | | |
|---|---|---|---|---|
| 5,707,818 A | * | 1/1998 | Chudzik et al. | ............ 435/7.93 |
| 5,731,212 A | * | 3/1998 | Gavin et al. | .................. 436/526 |
| 5,981,298 A | * | 11/1999 | Chudzik et al. | ............. 436/514 |
| 6,214,629 B1 | * | 4/2001 | Freitag et al. | ................ 436/518 |
| 6,297,020 B1 | * | 10/2001 | Brock | ......................... 435/7.1 |
| 7,315,378 B2 | * | 1/2008 | Phelan et al. | ................ 356/436 |
| 7,723,124 B2 | * | 5/2010 | Aberl et al. | .................... 436/518 |
| 2005/0036148 A1 | * | 2/2005 | Phelan | ....................... 356/446 |
| 2005/0130120 A1 | | 6/2005 | Lambotte et al. | |
| 2005/0196875 A1 | | 9/2005 | Blatt et al. | |
| 2005/0208593 A1 | | 9/2005 | Vail et al. | |
| 2007/0081920 A1 | | 4/2007 | Murphy et al. | |
| 2009/0061534 A1 | * | 3/2009 | Sharrock | ..................... 436/518 |

FOREIGN PATENT DOCUMENTS

GB        2402474        12/2004
WO   WO-2004/021004     3/2004

* cited by examiner

*Primary Examiner*—Bao-Thuy L Nguyen
(74) *Attorney, Agent, or Firm*—Foley Hoag LLP

(57) ABSTRACT

Disclosed is an assay device for determining the presence and/or extent of one or more analytes in liquid sample containing a) first and second assays each comprising a flow-path having a detection zone for immobilising a labelled binding reagent, wherein detection of a labelled binding reagent at one or both detection zones is indicative of the presence and/or extent of one or more analytes; b) a shared reference zone; c) one or more light sources to illuminate the detection zones and the reference zone; d) one or more photodetectors to detect light from the detection zones and the reference zone, which photodetector/s generate a signal, the magnitude of which signal is related to the amount of light detected; and e) signal processing means for processing signals from the photodetector/s.

27 Claims, 7 Drawing Sheets

32

31

53    57

ASSAY DEVICE WITH SHARED ZONES

RELATED APPLICATIONS

The present application claims benefit of priority to U.S. Provisional Patent Application No. 60/991,543, filed on Nov. 30, 2007; Great Britain Application 0809994.7, filed May 31, 2008; and Great Britain Application 0717045.9, filed Sep. 1, 2007, the contents of which are incorporated by reference herein in their entireties.

FIELD OF THE INVENTION

The present invention relates to an assay device, kit and method for determining the presence or extent of an analyte. In particular it relates to the determination of an analyte over an extended concentration range.

BACKGROUND OF THE INVENTION

Simple lateral flow immunoassay devices have been developed and commercialised for detection of analytes in fluid samples, see for example EP291194. Such devices typically comprise a porous carrier comprising a dried mobilisable labelled binding reagent capable of binding to the analyte in question, and an immobilised binding reagent also capable of binding to the analyte provided at a detection zone downstream from the labelled binding reagent. Detection of the immobilised labelled binding reagent at the detection zone provides an indication of the presence of analyte in the sample.

Alternatively, when the analyte of interest is a hapten, the immunoassay device may employ a competition reaction wherein a labelled analyte or analyte analogue competes with analyte present in the sample for an immobilised binding reagent at a detection zone. Alternatively the assay device may employ an inhibition reaction whereby an immobilised analyte or analyte analogue is provided a detection zone, the assay device comprising a mobilisable labelled binding reagent for the analyte.

An assay device may determine more than one analyte. For example in the case of assays for the determining the presence of drugs of abuse, the device may be capable of determining a whole panel of drugs. Such lateral flow immunoassay devices are provided with multiple detection zones, such zones being provided on a single or multiple lateral flow carriers.

Determination of the result of the assay has been traditionally carried out by eye. However such devices require the result to be interpreted by the user which introduces an undesirable degree of subjectivity.

As such, digital devices have been developed comprising an optical detection means arranged to determine the result of the assay as well as a display means to display the result of the assay. Digital assay readers for use in combination with assay test-strips for determining the concentration and/or amount of analyte in a fluid sample are known as are assay devices comprising an integral digital assay reader.

Light from a light source, such as a light emitting diode (LED), is shone onto a portion of the porous carrier and either reflected or transmitted light is detected by a photodetector. Typically, the reader will have more than one LED to illuminate various zones of the carrier, and a corresponding photodetector is provided for each of the plurality of LEDs. EP1484601 discloses an optical arrangement for a lateral flow test strip digital reading device comprising a baffle arrangement allowing for the possibility of reducing the number of photodetectors in the device.

Such devices are often designed to be single use and therefore it is desirable to keep the costs of such devices as low as possible, especially where expensive optical and electronic components are involved.

SUMMARY OF THE INVENTION

It is an object according to an aspect of the invention to provide an assay device having one or more shared zones enabling a reduction in the number of optical components that are required for an assay device comprising two or more assay flow-paths.

According to a first aspect, the invention provides an assay device for determining the presence and/or extent of one or more analytes in a liquid sample comprising:

a) first and second assays each comprising a flow-path having a detection zone for immobilising a labelled binding reagent, wherein detection of a labelled binding reagent at one or both detection zones is indicative of the presence and/or extent of one or more analytes;

b) a shared reference zone;

c) one or more light sources to illuminate the detection zones and the reference zone;

d) one or more photodetectors to detect light from the detection zones and the reference zone, which photodetector/s generate a signal, the magnitude of which signal is related to the amount of light detected; and e) signal processing means for processing signals from the photodetector/s.

It is a further object of the invention to provide an assay reader for use with one or more assay test-strips comprising two or more assay flow-paths, the assay reader having a reduction in the number of optical components that are typically required.

According to a second aspect, the invention provides an assay reader for reading the result of first and second assays each comprising a flow-path, each flow-path comprising a detection zone for immobilising labelled binding reagent, wherein detection of labelled binding reagent at one or both detection zones is indicative of the presence and/or extent of one or more analytes, and a shared reference zone; said assay reader comprising:

a) one or more light sources to illuminate the detection zones, and the shared reference zone;
   b) one or more photodetectors to detect light from the detection zones and the reference zone, which photodetector/s generate a signal, the magnitude of which signal is related to the amount of light detected; and signal processing means for processing signals from the photodetector/s, wherein the signal obtained from the shared reference zone is used to compensate the values of the signals obtained from the detection zones.

The first and/or second assay may comprise a labelled binding reagent provided in a mobilisable form upstream from the detection zone in a dry state prior to use of the device.

The shared reference zone may be comprised as part of either the first or second assay. Alternatively the reference zone may be provided on a subsidiary flow-path to the first and second assay. The reference zone may be chosen from a portion of the flow-path not corresponding to a detection zone, or, where a dried labelled reagent is present upstream from the detection zone, a portion not corresponding to where the dried labelled reagent is present. The reference zone may be provided downstream or upstream from the detection zone. Measurement of the reference zone enables measurement of the background levels of reflected or transmitted light from the flow-path. The background level may be affected by, for example, the optical reflectance of the porous carrier, the presence of liquid sample, or of components of the assay such as a labelled binding reagent. The levels of light measured at the detection zone may therefore be corrected with respect to the levels of background light to provide a compensated signal more accurately indicative of the amount of labelled binding reagent present at the detection zone. Measurement at the reference zone also compensates for any variation between fluid samples applied to assay devices, for example urine samples may vary widely in colour. The value of the signal obtained at the reference zone for one assay is used to compensate the value of the signal obtained at the detection zone for the other assay. As such the reference zone is "shared" between both assays. The provision of a shared reference zone can reduce the number of components required for the assay device, since each reference zone would typically require a light source.

The concept of a shared reference zone is rather counterintuitive. The purpose of a reference measurement is to allow for variations in the background readings of signals which can arise, inter alia, as a result of variations in reagent or assay strip composition. Accordingly, the normal practice is to use a separate reference zone on each assay, so that a "dedicated" reference measurement can be made for each assay.

The present inventors have found however that separate reference zones can be dispensed with and instead a single shared reference zone will suffice.

The light source is conveniently an LED. A plurality of LEDs may be employed. In an embodiment each zone in the assay (detection, reference or control zone) is illuminated by a respective LED. The one or more photodetectors may conveniently comprise a photodiode. In a preferred embodiment a single photodiode or other photodetector is employed. In one embodiment there are four LEDs and a single photodiode.

The assay device may further comprise a control zone which may be a single control zone provided as part of either the first or second assay. Alternatively the control zone may be provided on a subsidiary flow-path to the first and second assay. Provision of a single control zone reduces further the number of light sources that are needed. The purpose of the control zone is to indicate that the assay has been carried out correctly, namely that fluid sample has been applied to the device and that labelled binding reagent has moved along the flow-path to some extent. The control zone may be provided downstream from the detection zone. A suitable control zone is disclosed in EP291194 and may comprise an immobilised binding reagent for a labelled binding reagent. A separate population of labelled binding reagent may be provided upstream from the detection and control zones wherein said separate population of labelled binding reagent is capable of being immobilised at the control zone but does not become immobilised at the detection zone in the presence or absence of analyte. The control zone is typically provided downstream from the detection zone. The signal obtained at the control zone may also be referenced with respect to the signal obtained at the reference zone.

Thus measurement of the signal at the control zone provides a value or indication that the test has been carried out correctly (or incorrectly) for that assay. If for example, the control zone indicates that the test has been carried out correctly for one assay, an assumption is made that the test has been carried out correctly at the other assay. Hence the control zone may be thought of as being "shared" between the assays of the assay device. As in the case of a shared reference zone, provision of a single or "shared" control zone enables a reduced number of optical components to be used in the device. The rationale for making this assumption is that it is highly likely that if liquid sample has been applied to one assay flow-path, that liquid sample has been applied to the other flow-path, especially so if the two assay flow-paths are connected, for example by a common sample receiving means such as a porous sample receiver. Furthermore, if the assay device has for example been subjected to conditions, such as ingress of moisture which may for example result in poor resuspension of the mobilisable reagents, or high temperature which may denature the binding reagents, it is likely that both flow-paths will be affected. As in the case of a shared reference zone, the concept of a shared control is also counterintuitive. The signal at the control zone is calculated with respect to the signal at the reference zone.

The reference and control zones may be provided as part of the same assay or provided as part of different assays. In an exemplary embodiment, the shared reference and control zones are each provided in separate assays, e.g. one assay comprises a detection zone and a reference zone, and the other assay comprises a detection zone and a control zone.

According to a third aspect the invention provides an assay device for determining the presence and/or extent of one or more analytes in a liquid sample comprising:

a) first and second assays each comprising a flow-path having a detection zone for immobilising a labelled binding reagent, wherein detection of a labelled binding reagent at one or both detection zones is indicative of the presence and/or extent of one or more analytes;

b) a shared control zone;

c) one or more light sources to illuminate the detection zones and the control zone;

d) one or more photodetectors to detect light from the detection zones and the control zone, which photodetector/s generate a signal, the magnitude of which signal is related to the amount of light detected; and e) signal processing means for processing signals from the photodetector/s.

According to a fourth aspect, the invention provides an assay reader for reading the result of first and second assays each comprising:

a flow-path, each flow-path comprising a detection zone for immobilising labelled binding reagent, wherein detection of labelled binding reagent at one or both detection zones is indicative of the presence and/or extent of one or more analytes; and a shared control zone;

said assay reader comprising:
   a) one or more light sources to illuminate the detection zones, and the shared control zone;
   b) a stored control signal threshold
   c) one or more photodetector/s to detect light from the detection zones and the control zone, which photodetector/s generate a control signal and detection signals, the magnitude of which signals are related to the amount of light detected; and
   d) signal processing means to process signals from the photodetector/s and to compare the signal obtained from the control zone to the control signal threshold, and to determine that both assays have been carried out correctly if the control signal is equal to or greater than the control signal threshold.

The assay device and reader according to the first, second and third aspects of the invention may comprise a control signal threshold.

The control signal threshold may be stored in the device or reader. The signal measured from the control zone may be compared to the control signal threshold to determine whether sufficient labelled binding reagent has become immobilised at said zone. If the value of the control signal is equal to or exceeds the control signal threshold, the device or reader may determine that the assay has been carried out satisfactorily. If the control signal is less than the control signal threshold, the device or reader may determine that the assay has been not been carried out satisfactorily and will provide an error message.

The signal detected from the control zone may be referenced to a signal obtained from a reference zone.

The assay device according to the third aspect may also comprise a shared reference zone.

The first and/or second assay may conveniently comprise a binding reagent for an analyte or a labelled binding reagent provided in an immobilised form at the detection zone.

By employing a shared reference and/or a shared control zone, the assay device of the invention provides for reduced number of zones that need to be interrogated and consequently the number of optical components that need to be employed. The use of shared zones is most effective when the assay architectures of the first and second assays are very similar or, if the reference and/or control zone is provided on one or more subsidiary flow-paths, when the assay architecture of the one or more subsidiary flow-paths is similar to the first and second assays. Thus, for example, the assays will typically both comprise porous carriers of similar material (e.g. both comprise nitrocellulose carriers). It is also advantageous to use the same liquid sample for each assay. This may be conveniently achieved by providing a common sample application region that is in fluid communication with both assays. Thus a single liquid sample applied to the device via the common sample application region may flow through both the first and second assays. In cases where the first and second assays are non-identical, it may be acceptable to provide a shared reference zone as long as background levels of light that would be detected at each assay are sufficiently similar to each other.

The signal processing means may comprise a central processor unit which is able to process the signals obtained from the photodetectors from the respective zones and calculate values obtained at the test zone with respect to the reference zone. The measurement data may be taken at various times during the assay and may be taken after the device has been switched on but before fluid sample has been applied to the device, in order to obtain optical values of light transmission or reflectance in the dry state.

An absorbent "sink" can be provided at the distal end of the assay flow-paths. A common sink may be provided or a sink may be provided at the distal end of each assay. The absorbent sink may preferably comprise a highly absorbent material such as, for example, CF7 Whatman paper, and should provide sufficient absorptive capacity to remove any unbound conjugate from the vicinity of the detection zones, the reference zone and the control zone. As an alternative to such a sink it can be sufficient to have a length of porous solid phase material which extends beyond the detection zone. An advantage of providing a highly absorbent sink is that it removes or substantially removes excess labelled binding reagent from the flow-paths of the respective assays. This has the effect of minimising the extent of unbound labelled binding reagent in the vicinity of respective zones and therefore enables assay flow paths to be employed in the device that may have differing amounts of labelled binding reagent.

As an alternative to providing an immobilised binding reagent at the detection zone, the binding reagent may be provided in a mobilisable form which is capable of binding to an analyte-labelled binding reagent complex. The binding reagent may for example be conjugated to a large particle such as agarose and the detection zone may comprise a filter whose pore-size has dimensions smaller than the large particle, but larger than the size of the labelled binding reagent, such that the filter is able to trap any labelled binding reagent/analyte/binding reagent complex present, any labelled binding reagent that is not complexed to the capture reagent being able to pass through the filter. Yet alternatively a reagent may be provided in an immobilised form at the detection zone that is capable of binding a mobilisable labelled binding reagent/analyte/binding reagent complex. For example the binding reagent may be provided in a mobilisable form and conjugated to a binding species such as biotin, the reagent immobilised at the detection zone being a complementary binding partner such as streptavidin.

The assay device may employ a sandwich immunoassay and/or a competitive/inhibition assay for the determination of an analyte. An example of a sandwich immunoassay is where a labelled binding reagent/analyte/binding reagent complex is formed. The device will typically comprise a labelled binding reagent for the analyte in a mobilisable form provided upstream from a detection zone comprising an immobilised binding reagent for the analyte. Alternatively, in particular when the analyte of interest is a hapten, the immunoassay device may employ a competition reaction wherein a labelled analyte or labelled analyte analogue competes with analyte present in the sample for an immobilised binding reagent at a detection zone. The labelled analyte or labelled analyte analogue may be provided in a mobilisable form upstream from the detection zone. Yet alternatively the assay device may employ an inhibition reaction wherein an immobilised analyte or analyte analogue is provided at detection zone, the assay device comprising a mobilisable labelled binding reagent for the analyte.

The term "flow-path" for the purposes of this invention refers to a substrate that is able to convey a liquid from a first position to a second position and may be for example a capillary channel, a microfluidic pathway, or a porous carrier such as a lateral flow porous carrier. The porous carrier may comprise one or a plurality of porous carrier materials which may overlap in a linear or stacked arrangement or which are fluidically connected. The porous carrier materials may be the same or different. The first and second assays may be provided on separate substrates or they may be provided on a common substrate such that liquid being conveyed along a flow-path of the first assay is not able to cross over to the flow-path of the second assay. For example, the first and second assays may be provided on the same porous carrier such that the first and second flow-paths are isolated from each other. This may be achieved for example by laser cutting parts of the porous carrier to make it non-porous, thus separating the first and second assays. Alternatively, a non-porous blocking material may be applied along a strip to provide two (typically essentially parallel) flow paths on the same porous carrier.

In particular the flow-path may be a lateral flow porous carrier. Suitable materials that may be employed as a porous carrier include nitrocellulose, acetate fibre, cellulose or cellulose derivatives, polyester, polyolefin or glass fibre. The porous carrier may comprise nitrocellulose. This has the advantage that a binding reagent can be immobilised firmly without prior chemical treatment. If the porous solid phase material comprises paper, for example, the immobilisation of the antibody in the second zone needs to be performed by chemical coupling using, for example, CNBr, carbonyldiimidazole, or tresyl chloride.

The term "binding reagent" refers to a member of a binding pair, i.e., two different molecules wherein one of the molecules binds with the second molecule through chemical and/or physical means. The two molecules are related in the sense that their binding with each other is such that they are capable of distinguishing their binding partner from other assay constituents having similar characteristics. The members of the binding pair are referred to as ligand and receptor (antiligand), a binding pair member and binding pair partner, and the like. A molecule may also be a binding pair member for an aggregation of molecules; for example an antibody raised against an immune complex of a second antibody and its corresponding antigen may be considered to be an binding pair member for the immune complex.

In addition to antigen and antibody binding pair members, other binding pairs include, as examples without limitation, biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders (e.g., ribonuclease, S-peptide and ribonuclease S-protein), and the like. Furthermore, specific binding pairs can include members that are analogues of the original specific binding member.

"Label" when used in the context of a labelled binding reagent, refers to any substance which is capable of producing a signal that is detectable by visual or instrumental means. Various labels suitable for use in the present invention include labels which produce signals through either chemical or physical means, such as being optically detectable. Such labels include enzymes and substrates, chromogens, catalysts, fluorescent compounds, chemiluminescent compounds, electroactive species, dye molecules, radioactive labels and particle labels. The analyte itself may be inherently capable of producing a detectable signal. The label may be covalently attached to the binding reagent. In particular the label may be chosen from one that is optically detectable.

The label may comprise a particle such as gold, silver, colloidal non-metallic particles such as selenium or tellurium, dyed or coloured particles such as a polymer particle incorporating a dye, or a dye sol. The dye may be of any suitable colour, for example blue. The dye may be fluorescent. Dye sols may be prepared from commercially-available hydrophobic dyestuffs such as Foron Blue SRP (Sandoz) and Resolin Blue BBLS (Bayer). Suitable polymer labels may be chosen from a range of synthetic polymers, such as polystyrene, polyvinyltoluene, polystyrene-acrylic acid and polyacrolein. The monomers used are normally water-insoluble, and are emulsified in aqueous surfactant so that monomer micelles are formed, which are then induced to polymerise by the addition of initiator to the emulsion. Substantially spherical polymer particles are produced. An ideal size range for such polymer particles is from about 0.05 µm to about 0.5 µm. According to an exemplary embodiment the label is a blue polymeric particle.

The dried binding reagents may be provided on a porous carrier material provided upstream from a porous carrier material comprising the detection zone. The upstream porous carrier material may be macroporous. The macroporous carrier material should be low or non-protein-binding, or should be easily blockable by means of reagents such as BSA or PVA, to minimise non-specific binding and to facilitate free movement of the labelled reagent after the macroporous body has become moistened with the liquid sample. The macroporous carrier material can be pre-treated with a surface active agent or solvent, if necessary, to render it more hydrophilic and to promote rapid uptake of the liquid sample. Suitable materials for a macroporous carrier include plastics materials such as polyethylene and polypropylene, or other materials such as paper or glass-fibre. In the case that the labelled binding reagent is labelled with a detectable particle, the macroporous body may have a pore size at least ten times greater than the maximum particle size of the particle label. Larger pore sizes give better release of the labelled reagent. As an alternative to a macroporous carrier, the labelled binding reagent may be provided on a non-porous substrate provided upstream from the detection zone, said non-porous substrate forming part of the flow-path.

The porous carrier may comprise a glass-fibre macroporous carrier provided upstream from and overlapping at its distal end a nitrocellulose porous carrier.

The liquid sample can be derived from any source, such as an industrial, environmental, agricultural, or biological source. The sample may be derived from or consist of a physiological source including blood, serum, plasma, interstitial fluid, saliva, sputum, ocular lens liquid, sweat, urine, milk, mucous, synovial liquid, peritoneal liquid, transdermal exudates, pharyngeal exudates, bronchoalveolar lavage, tracheal aspirations, cerebrospinal liquid, semen, cervical mucus, vaginal or urethral secretions and amniotic liquid. In particular the source may be human and in particular the sample may be urine.

"Light" as used herein is intended to encompass any suitable electromagnetic radiation, regardless of wavelength. Notwithstanding this, the invention is primarily intended to utilise light in the visible part of the spectrum, and "light source" and "photodetector" should be construed accordingly as encompassing respectively any source of, and means for detecting, electromagnetic radiation, but especially relating to radiation of visible wavelengths (i.e. in the range of about 390-800 nm).

The photodetector/s will detect light from one or more zones of the assay device. The light may actually originate from those zones, for example, if the label is fluorescent or the like. More normally however, the photodetector/s will detect light which appears to emanate from those zones i.e., light which originates from the light source and is reflected and/or transmitted by the zone onto the photodetector.

Analytes include, but are not limited to, toxins, organic compounds, proteins, peptides, micro-organisms, bacteria, viruses, amino acids, nucleic acids, carbohydrates, hormones, steroids, vitamins, drugs (including those administered for therapeutic purposes as well as those administered for illicit purposes), pollutants, pesticides, and metabolites of or antibodies to any of the above substances. The term analyte also includes any antigenic substances, haptens, antibodies, macromolecules, and combinations thereof.

The assay device may determine one or more analytes.

The assay device may be capable of determining the amount or presence of an analyte over an extended analyte range, wherein the first assay is capable of determining the level of analyte at a lower concentration range and the second assay is capable of determining the level of analyte in a liquid sample at a higher concentration range.

There are several ways in which an assay may be prepared in order to measure analyte at a higher analyte range.

For example, the assay device may comprise a scavenger assay comprising a labelled binding reagent for the analyte and a scavenger binding reagent for the analyte, provided upstream from the detection zone. The scavenger binding reagent serves to remove excess analyte and lower the sensitivity of the assay. This has the effect of increasing the dynamic range of the assay enabling measurement at higher analyte levels. The scavenger binding reagent may be may be immobilised, mobilisable or both. The scavenger binding reagent may be provided at either the same region of the porous carrier as the mobilisable labelled binding reagent, upstream from it or downstream from it. The scavenger binding reagent may bind to the same binding region of the analyte as the mobilisable labelled binding reagent or to a different region of the analyte than the labelled binding reagent. The scavenger reagent may have a different affinity for the analyte than the mobilisable labelled binding reagent of the second assay. In an exemplary embodiment, the scavenger binding reagent has a higher affinity for the analyte than the mobilisable binding reagent of the second assay. The amount of scavenger binding reagent may be varied to change the sensitivity of the assay to analyte concentration. Increasing the amount of scavenger binding reagent present lowers the sensitivity of the assay due to the fact that the scavenger binding reagent is able to bind more analyte, effectively lowering the proportion of labelled binding reagent that is able to bind to the detection zone.

In order to increase the dynamic range of the assay, the assay device may for example comprise multiple detection zones, wherein each detection zone is capable of binding analyte at different analyte concentration levels. For example the respective zones may comprise binding reagent for the analyte having a differing affinities for the analyte.

Other ways to increase the dynamic range of the assay are to provide an assay device comprising a sandwich binding assay and a competition or inhibition assay. For example, the sandwich assay may be the high sensitivity assay, namely it is capable of measuring analyte at a lower concentration range and the inhibition or competition assay may be a low sensitivity assay, namely it is capable of measuring analyte at a higher concentration range. A further way is to alter the affinity or amount of the labelled binding reagent or the immobilised reagent at the detection zone. A high affinity binding reagent will have a higher analyte sensitivity than a lower affinity binding reagent. Similarly a low concentration of binding reagent will have a lower analyte sensitivity than a high concentration of binding reagent. The assay sensitivity can be changed by altering the ratio of binding reagent to the label of the labelled binding reagent. If a particle is used as the label, then the quantity of the binding reagent applied to the label can be altered to alter assay sensitivity. A further way to manipulate the sensitivity of an assay is to vary the quantity of the label used in the assay. For example the sensitivity of an assay may be lowered by reducing the ratio of binding reagent to labelled species for the labelled binding reagent.

A further means of manipulating the sensitivity of an assay is to alter the optical density of a label. The assay sensitivity can be lowered by use of a label with a low optical density. This may be achieved for example by provision of a polymer particle label having a low concentration of dye or by use a coloured label which is less sensitive to an optical detector.

Yet a further way to measure high analyte levels is to employ a non-particulate labelled binding reagent. High levels of analyte when measured by way of a sandwich binding assay require high levels of binding reagent. In the case wherein the label is a particle label, provision of high levels of analyte within or on the porous carrier can give rise to steric hindrance resulting in poor assay sensitivity. Conversely, at lower analyte levels, the use of a non-particle labelled binding reagent can give rise to a low signal due to the low optical density. However, at high analyte levels, non-particle labels may be present at sufficiently high levels to be readily detected. An example of a optically detectable non-particulate label may be a dye. The dye may be fluorescent.

Assay sensitivity may be influenced by the flow rate of the porous carrier. A way to lower the sensitivity of the assay is to employ a porous carrier (such as nitrocellulose) having a higher flow rate.

The sensitivity of an assay may be further manipulated by modifying the rate at which the labelled binding reagent is released from its origin. A further way to lower analyte sensitivity is to provide for a rapid release of the labelled binding reagent from the porous carrier during contact with the liquid sample. The release of the labelled binding reagent can be modified by the provision of sugars, proteins or other polymeric substances such as methylcellulose within the device.

According to a particular embodiment, the assay device comprises a scavenger assay comprising a mobilisable second (scavenger) binding reagent for the analyte and a mobilisable binding reagent for the analyte provided upstream from the detection zone.

According to a particular embodiment the first assay is capable of measuring analyte in a lower analyte concentration range and the second assay is capable of measuring analyte in a higher analyte concentration range. The first assay may comprise a shared reference zone and the second assay may comprise a shared control zone.

The first assay may comprise a labelled binding reagent provided upstream from a detection zone and the second assay may comprise a labelled binding reagent and a mobilisable scavenger binding reagent provided upstream from a detection zone. The scavenger binding reagent may be provided at the same position or in the region of the labelled binding reagent upstream from the detection zone.

In particular the analyte to be determined is hCG and the liquid sample is urine.

In order to measure an analyte concentration over a certain range it is important to ensure that there is sufficient labelled binding reagent present such that the assay signal does not become saturated. Measurement of large amounts of analyte often requires a corresponding increase in the amount of labelled binding reagent to avoid the so-called "hook effect" or saturation of the assay signal with increasing analyte concentration. Variation in the control signal has been shown to occur particularly in the case where there is an increased amount of binding reagent present.

Where first and second assays are provided having differing amounts of labelled binding reagent, it has been shown to be advantageous to provide the reference zone as part of the assay having a lower level of labelled binding reagent.

According to an embodiment, the assay device is capable of measuring analyte at a higher analyte range. There are several ways of providing such a device.

For example, the assay device may comprise a labelled binding reagent for the analyte and a second binding reagent for the analyte, provided upstream from the detection zone. The second binding reagent serves to remove excess analyte and lower the sensitivity of the assay. This has the effect of increasing the dynamic range of the assay enabling measurement at higher analyte levels. The second binding reagent may be may be immobilised, mobilisable or both. The second binding reagent may be provided at either the same region of the porous carrier as the mobilisable labelled binding reagent, upstream from it or downstream from it. The second binding reagent may bind to the same binding region of the analyte as the mobilisable labelled binding reagent or to a different region of the analyte than the labelled binding reagent. The second reagent may have a different affinity for the analyte than the mobilisable labelled binding reagent of the second assay. In an exemplary embodiment, the second binding reagent has a higher affinity for the analyte than the mobilisable binding reagent of the second assay. The amount of second binding reagent may be varied to change the sensitivity of the assay to analyte concentration. Increasing the amount of second binding reagent present lowers the sensitivity of the assay due to the fact that the second binding reagent is able to bind more analyte, effectively lowering the proportion of labelled binding reagent that is able to bind to the detection zone.

In order to increase the dynamic range of the assay, the assay device may for example comprise multiple detection zones, wherein each detection zone is capable of binding analyte at different analyte concentration levels. For example the respective zones may comprise binding reagent for the analyte having a differing affinities for the analyte.

Other ways to increase the dynamic range of the assay are to provide an assay device comprising a sandwich binding assay and a competition or inhibition assay. For example, the sandwich assay may be the high sensitivity assay, namely it is capable of measuring analyte at a lower concentration range and the inhibition or competition assay may be a low sensitivity assay, namely it is capable of measuring analyte at a higher concentration range. A further way is to alter the affinity or amount of the labelled binding reagent or the immobilised reagent at the detection zone. A high affinity binding reagent will have a higher analyte sensitivity than a lower affinity binding reagent. Similarly a low concentration of binding reagent will have a lower analyte sensitivity than a high concentration of binding reagent. The assay sensitivity can be changed by altering the ratio of binding reagent to the label of the labelled binding reagent. If a particle is used as the label, then the quantity of the binding reagent applied to the label can be altered to alter assay sensitivity. A further way to manipulate the sensitivity of an assay is to vary the quantity of the label used in the assay. For example the sensitivity of an assay may be lowered by reducing the ratio of binding reagent to labelled species for the labelled binding reagent.

A further means of manipulating the sensitivity of an assay is to alter the optical density of a label. The assay sensitivity can be lowered by use of a label with a low optical density. This may be achieved for example by provision of a polymer particle label having a low concentration of dye or by use a coloured label which is less sensitive to an optical detector.

Yet a further way to measure high analyte levels is to employ a non-particulate labelled binding reagent. High levels of analyte when measured by way of a sandwich binding assay require high levels of binding reagent. In the case wherein the label is a particle label, provision of high levels of analyte within or on the porous carrier can give rise to steric hindrance resulting in poor assay sensitivity. Conversely, at lower analyte levels, the use of a non-particle labelled binding reagent can give rise to a low signal due to the low optical density. However, at high analyte levels, non-particle labels may be present at sufficiently high levels to be readily detected. An example of a optically detectable non-particulate label may be a dye. The dye may be fluorescent.

Assay sensitivity may be influenced by the flow rate of the porous carrier. A way to lower the sensitivity of the assay is to employ a porous carrier (such as nitrocellulose) having a higher flow rate.

The sensitivity of an assay may be further manipulated by modifying the rate at which the labelled binding reagent is released from its origin. A further way to lower analyte sensitivity is to provide for a rapid release of the labelled binding reagent from the porous carrier during contact with the liquid sample. The release of the labelled binding reagent can be modified by the provision of sugars, proteins or other polymeric substances such as methylcellulose within the device.

According to a particular embodiment, the assay device comprises a mobilisable second binding reagent for the analyte and a mobilisable binding reagent for the analyte provided upstream from the detection zone. The second binding reagent may be provided at the same or similar position upstream from the detection zone as the labelled binding reagent.

According to a particular embodiment, the assay device comprises two assays each comprising an flow-path, wherein the first assay is capable of measuring analyte in a lower analyte concentration range and the second assay is capable of measuring analyte in a higher analyte concentration range. The first assay may comprise a shared reference zone and the second assay may comprise a shared control zone.

The assay device of the invention may be used to measure the extent or presence of hCG over an extended concentration range. The range may vary from between about 10 mIU to about 250,000 mIU.

The second assay may comprise a labelled binding reagent for the analyte and a second binding reagent for the analyte. The first assay may comprise labelled binding reagent for the analyte provided upstream from the detection zone.

The assay device may comprise one or more further measurement threshold values to indicate the level of analyte in a certain analyte range. In an embodiment, the assay device comprises a first and second measurement thresholds, wherein an analyte measurement signal of less than the first measurement threshold is indicative of the absence of analyte or the absence of analyte above a certain level and wherein an analyte measurement signal greater than the second threshold is indicative of the level of analyte in a second concentration range and a measurement signal of less than the second threshold is indicative of the level of analyte in a first concentration range. According to a particular embodiment, the assay device additionally comprises a third measurement threshold, wherein an analyte measurement signal greater than the third threshold is indicative of the level of analyte in a third concentration range.

In particular the assay device may be capable of measuring the presence and extent of the analyte hCG analyte in a liquid sample, in particular urine, of a female mammalian subject. The assay device may comprise a first measurement threshold, wherein hCG analyte signal levels of below the threshold are indicative or being not pregnant and wherein hCG analyte signal levels greater than or equal to the first measurement threshold are indicative of being pregnant, wherein the device comprises at least a further measurement threshold. In addition the assay device may provide an indication of the extent of pregnancy. The assay device may provide a time-based indication to the user, such as the extent of pregnancy in units of days or weeks.

A typical full assay development time for an assay test for the determination of hCG in urine is 3 minutes.

It is an desirable object of the invention to reduce the number of optical components, this may be conveniently achieved, where the reference zone is provided as part of one assay and the control zone is provided as part of the other assay. According to an embodiment, the reference zone is provided as part of a first assay having a lower level of labelled binding reagent and the control zone is provided as part of a second assay having a higher level of binding reagent.

According to an embodiment, the assay device comprises four light sources, wherein the light sources are arranged to illuminate the detection zones of the first and second assay and the shared control and reference zones, each zone being illuminated by a respective light source. One or more photodetectors may be positioned to detect reflected and/or transmitted light from the respective zones. According to an embodiment, a single photodetector may be employed to detect light from all of the zones. This may be achieved by, for example, illuminating the respective zones sequentially such that the device is able to recognise from which zone light detected at the photodetector is emanating. The sequential illumination process may be repeated with a fixed or varied frequency during the duration of the assay such that the levels of signal over time at each zone may be monitored. In addition the change in levels of light detected from one or more zones may be used to determine whether and when a fluid sample has been applied to the device and to determine the flow-rate of liquid sample along the device. Determination of the flow-rate may be used as a further quality control check, for example the assay may be rejected if the flow-rate is either greater than or less than set levels. A suitable flow-rate detection method and means is disclosed by EP1484641.

The labelled binding reagent typically accumulates at the detection zone over a period of time for a sandwich immunoassay and thus the rate of increase of signal over time may be monitored. The device may determine the result after the signal has reached equilibrium or more typically before the reaction has reached equilibrium. The device may provide a quantitative result such as a individual value, a semi-quantitative result or range such as 1-10, 11-20 and so on, or a qualitative result such as YES/NO. The device may determine the result with respect to one or more signal thresholds. The device may have a fixed measurement time or provide an early result before the fixed measurement time has elapsed. An early result may for example be given in the case where the device determines that the signal level will never exceed a particular threshold or exceeds a particular threshold at an early stage. In these particular cases the device may call an early NO or YES measurement, indicating the absence or presence of analyte with respect to a particular base level (which may be zero). An assay device employing an early result determination method is disclosed by EP1464613.

The assay device may be used to determine whether a subject is pregnant or not (namely whether the liquid sample contains hCG above a certain level) and may also employ further thresholds indicating to the user the extent of pregnancy. The extent of pregnancy may be displayed in terms of a time-based or concentration-based measurement.

The assay device will typically comprise a housing. The housing may be fluid impermeable and constructed from a suitable plastics material, such as ABS. The assay device may further comprise a sample receiving member for receiving the fluid sample. The sample receiving member may extend from the housing.

The housing may be constructed of a fluid impermeable material. The housing will also desirably exclude ambient light. The housing or casing will be considered to substantially exclude ambient light if less than 10%, preferably less than 5%, and most preferably less than 1%, of the visible light incident upon the exterior of the device penetrates to the interior of the device. A light-impermeable synthetic plastics material such as polycarbonate, ABS, polystyrene, polystyrol, high density polyethylene, or polypropylene containing an appropriate light-blocking pigment is a suitable choice for use in fabrication of the housing. An aperture may be provided on the exterior of the housing which communicates with the assay provided within the interior space within the housing. Alternatively the aperture may serve to allow a porous sample receiver to extend from the housing to a position external from the housing.

Also provided within the housing will typically be a power source. The device will typically comprise a display means to display the result of the assay as well as a memory means to store data. Conveniently the display means comprises an LCD.

The display means may further display further information such as an error message, personal details, time, date, and a timer to inform the user how long the assay has been measured for. The information displayed by the assay may be indicated in words, numbers or symbols, in any font, alphabet or language, for example, "positive", "negative", "+", "−", "pregnant", "not pregnant", "see your doctor", "repeat the test".

The assay device may comprise a porous sample receiver in fluid connection with and upstream from the flow-path. The assay device may comprise more than one assay flow-path each comprising a detection zone, in which case a single porous sample receiver may be provided which is common to the multiple assay flow paths. Thus a fluid sample applied to the porous sample receiver of the device is able to travel along the flow-paths of the respective assays to the respective detection zones. The porous sample receiver may be provided within a housing or may at least partially extend out of said housing and may serve for example to collect a urine stream. The porous sample receiver may act as a fluid reservoir. The porous sample receiving member can be made from any bibulous, porous or fibrous material capable of absorbing liquid rapidly. The porosity of the material can be unidirectional (i.e. with pores or fibres running wholly or predominantly parallel to an axis of the member) or multidirectional (omnidirectional, so that the member has an amorphous sponge-like structure). Porous plastics material, such as polypropylene, polyethylene (preferably of very high molecular weight), polyvinylidene fluoride, ethylene vinylacetate, acrylonitrile and polytetrafluoro-ethylene can be used. Other suitable materials include glass-fibre. Provision of a common porous sample receiver enables a single sample to be provided simultaneously to the flow-paths of the first and second assays and further increases the effectiveness of providing a shared reference and/or shared control zone.

In a fifth aspect, the invention provides a method of performing an assay to determine the presence and/or extent of one or more analytes, the method comprising the step of contacting a liquid sample with an assay device in accordance with the first and third aspects of the invention.

OVERVIEW OF THE FIGURES

DETAILED DESCRIPTION

Figure 1:
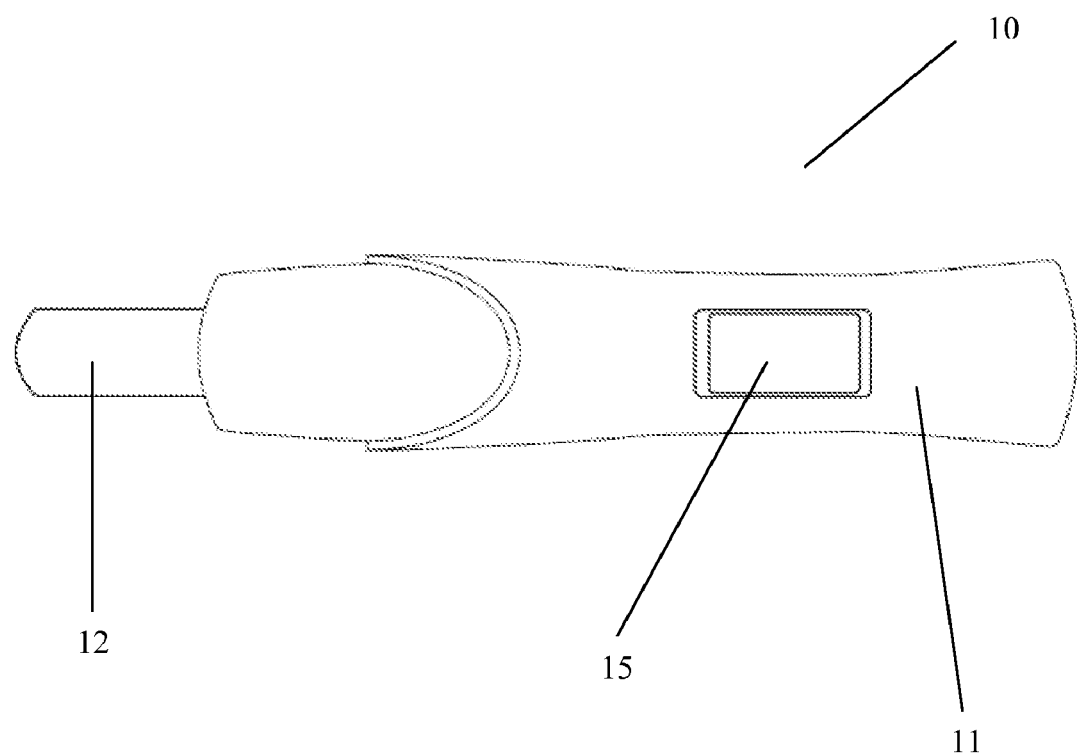
FIG. 1 is a view of an assay device in accordance with the invention.

An external top view of an assay device is shown in FIG. 1. The device (10) is elongate having a length of about 14 cm and a width of about 25 mm. The casing (11) may be formed of a suitable liquid impermeable casing such as polycarbonate, ABS, polystyrene, high density polyethylene, or polypropylene. The external porous sample receiver (12) may be formed of any bibulous, porous or fibrous material capable of absorbing liquid rapidly. Also shown is an LCD display (15) for displaying the results of the assay. Also provided within the assay device and not shown, are the assay flow-paths, light sources, photodetector, a power source and associated electronic components.

Figure 2:
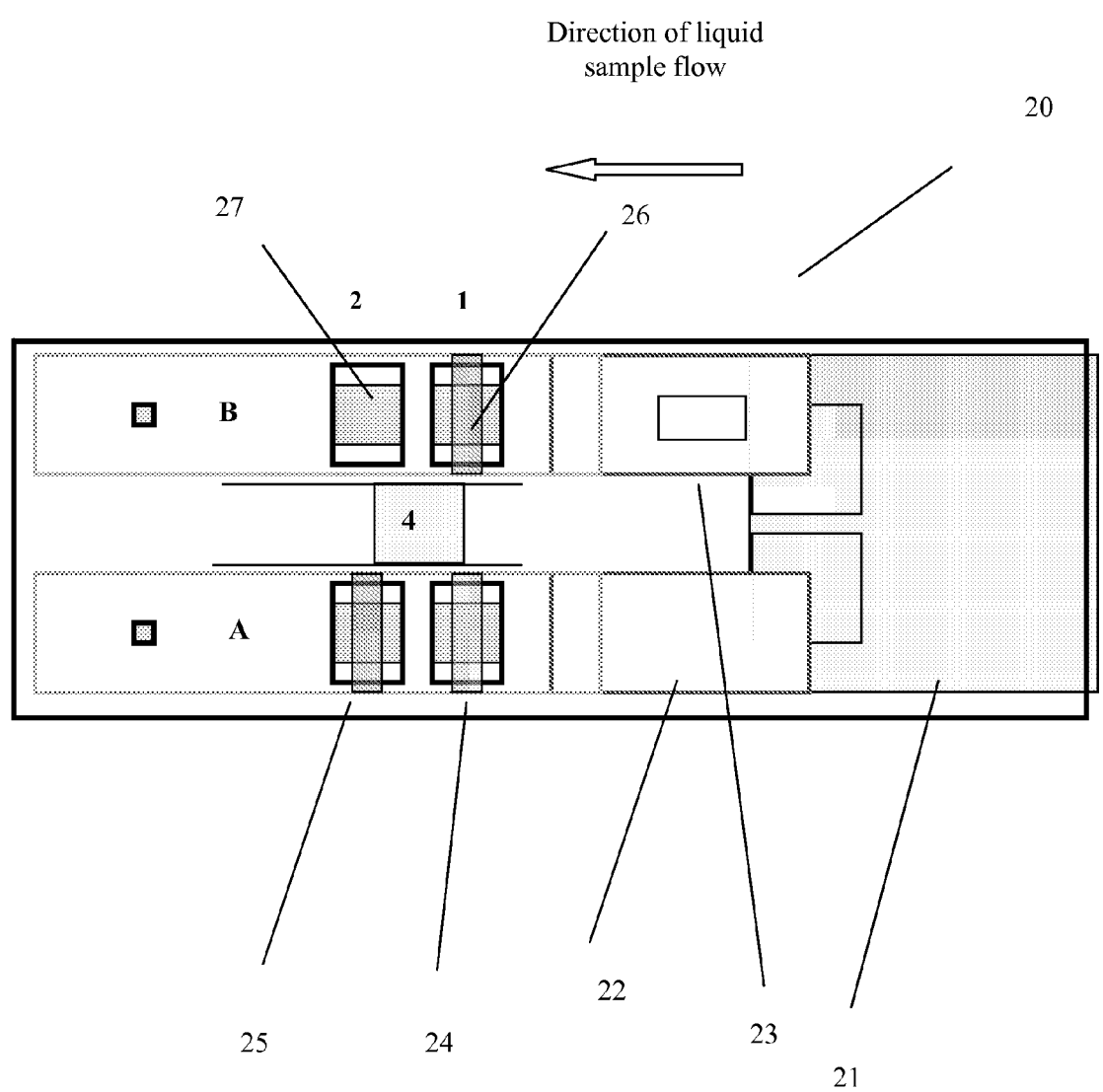
FIG. 2 is a schematic view of the assay flow-paths according to an exemplary embodiment in accordance with the invention.

FIG. 2 shows the layout of the photodetector and the individual assay porous carriers of an assay device according to an exemplary embodiment. Assay device (20) has a common sample application region (21) which fluidically connects first and second assays (22) and (23). A single photodetector (4) is provided between the two assays to detect light from the respective zones. Zones (24) and (25) correspond respectively to a detection and control zone on first assay (22). Zones (26) and (27) correspond respectively to a detection and reference zone on second assay (23). Not shown are the corresponding four LEDs which each illuminate a respective zone through appropriately positioned windows.

Figure 3:
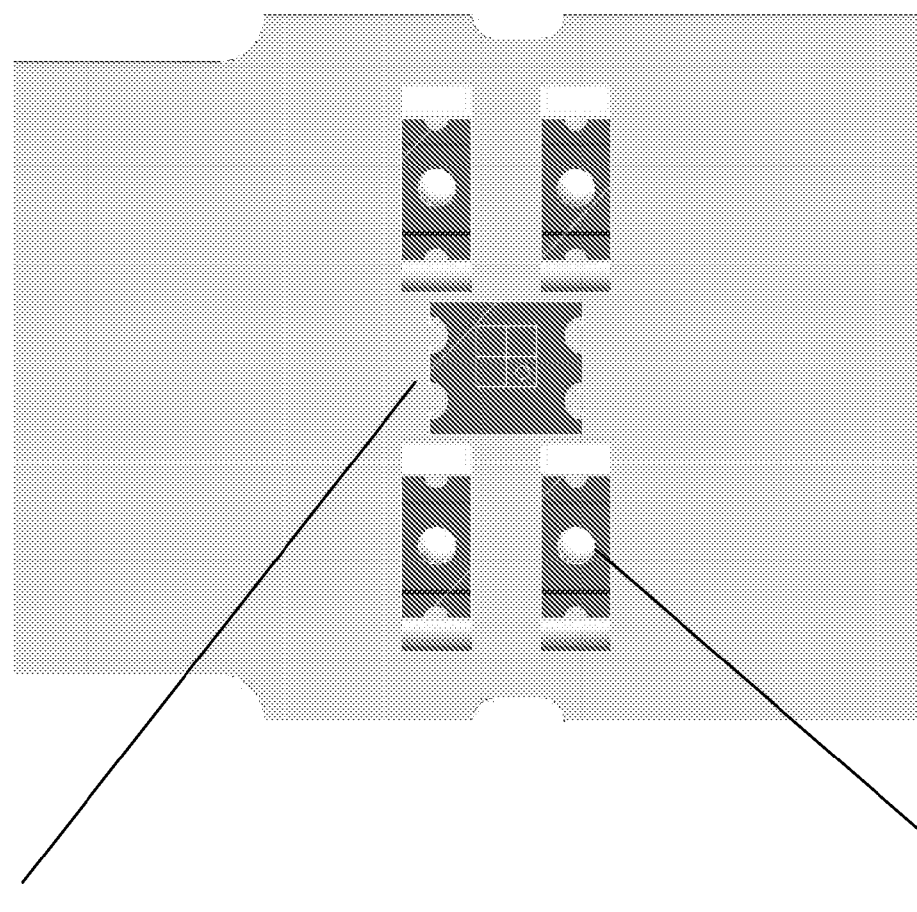
FIG. 3 is a view of the arrangement of light sources and photodetector of the embodiment shown in FIG. 2.

FIG. 3 shows a view of the arrangement according to an exemplary embodiment comprising a single photodetector (32) and four LEDs (31). The active area of the photodetector is 1.5 mm×1.5 mm.

Figure 4:
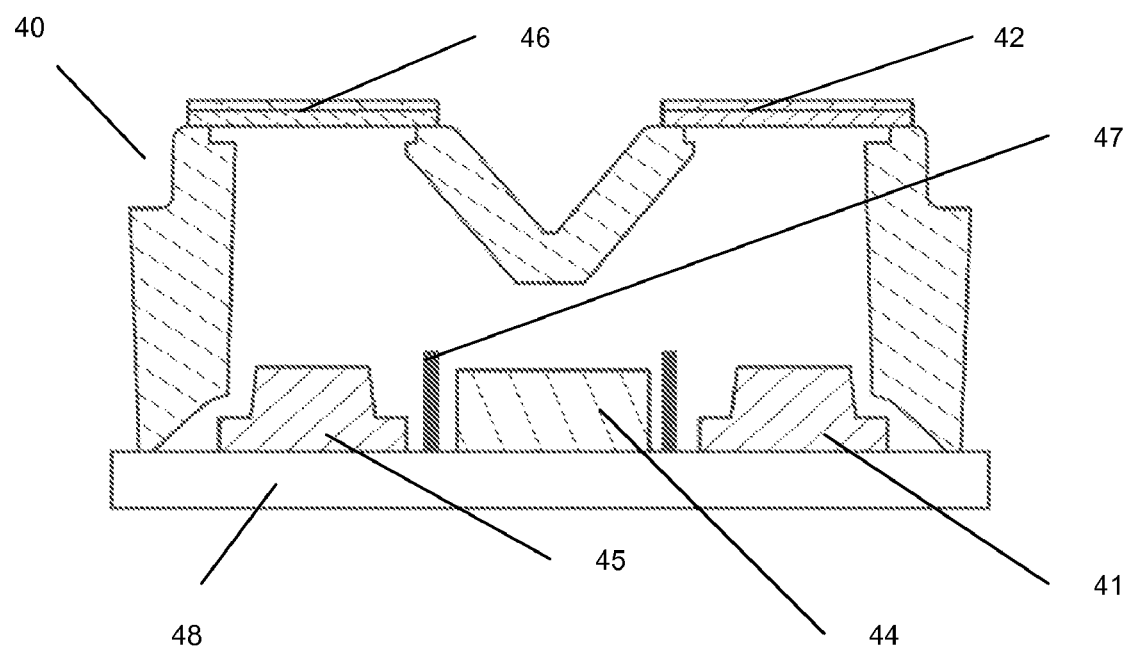
FIG. 4 is a schematic cross-sectional view of part of one embodiment of the assay device illustrating the relative positions of some of the assay components.

FIG. 4 shows a cross-sectional schematic view of the assay device (40) showing the relative positions of some of the components. Light from LED (41) illuminates a zone of strip (42) and light reflected from the zone is detected by the photodetector (44). Similarly, light from LED (45) illuminates a zone of strip (46) and reflected light is detected by the photodetector. Provided are dividers (47) which prevent light from the LED being directly incident on the photodetector. Also provided is a sloping member (48) which serves to prevent illumination of strip (46) by LED (41) and correspondingly the illumination of strip (42) by LED (45) whilst allowing light reflected from the respective test strips to be detected by the photodetector. The sloping member also serves to guide reflected light from the test-strips onto the photodetector. The LEDs are mounted on a surface (49) made from printed circuit board.

Figure 5A:
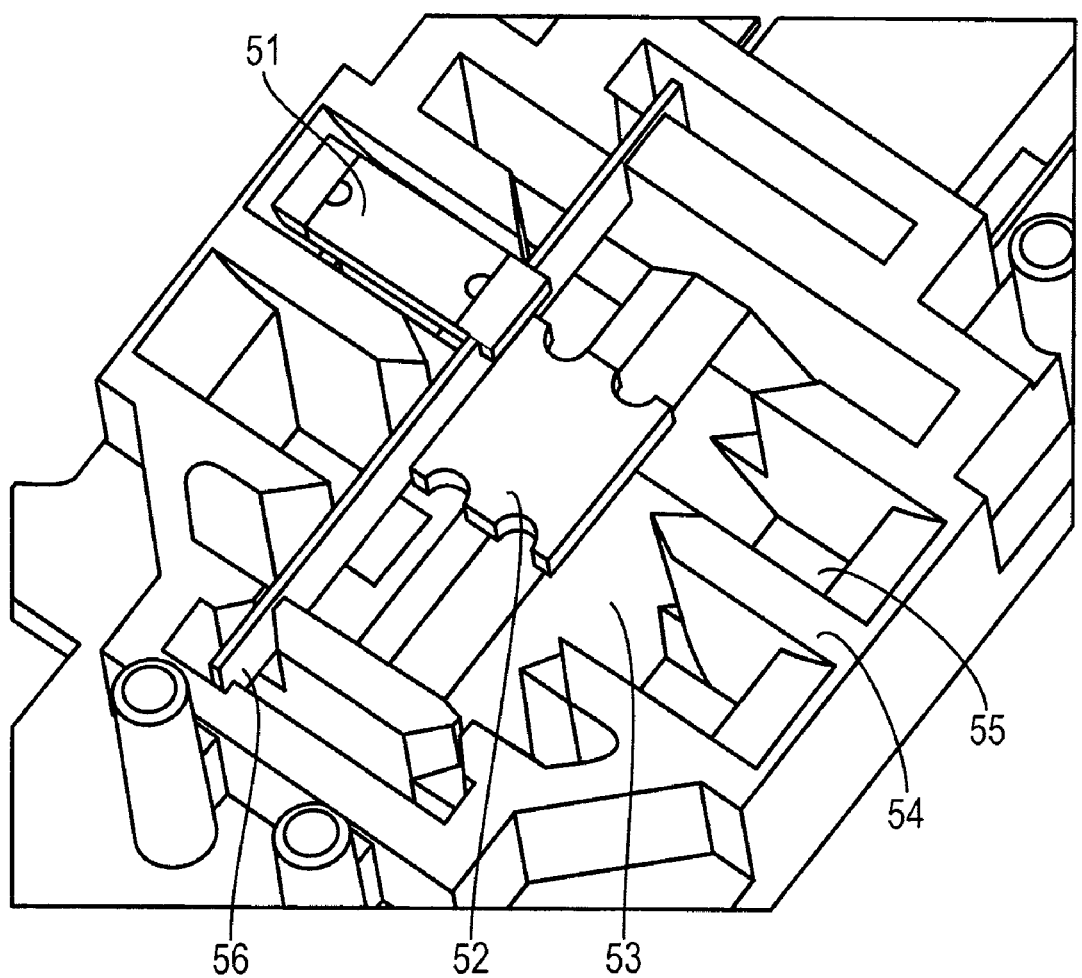
FIGS. 5a and 5b are views of the underside of a baffle arrangement also showing some of the optical components of the embodiment shown in FIG. 3.

FIG. 5a illustrates an underside view of the baffle arrangement of the exemplified embodiment. Light from the LEDs, of which one (denoted by reference numeral 51) is shown, illuminates a zone of an assay strip (not shown) through an aperture. Each LED is associated with a respective aperture. In the Figure, an exemplary aperture is denoted by reference numeral 55. Light is reflected from the strip onto photodetector (52). Also shown is the sloping member (53) and divider (56). Adjacent LEDs are screened from one another by baffles (54).

Figure 5B:
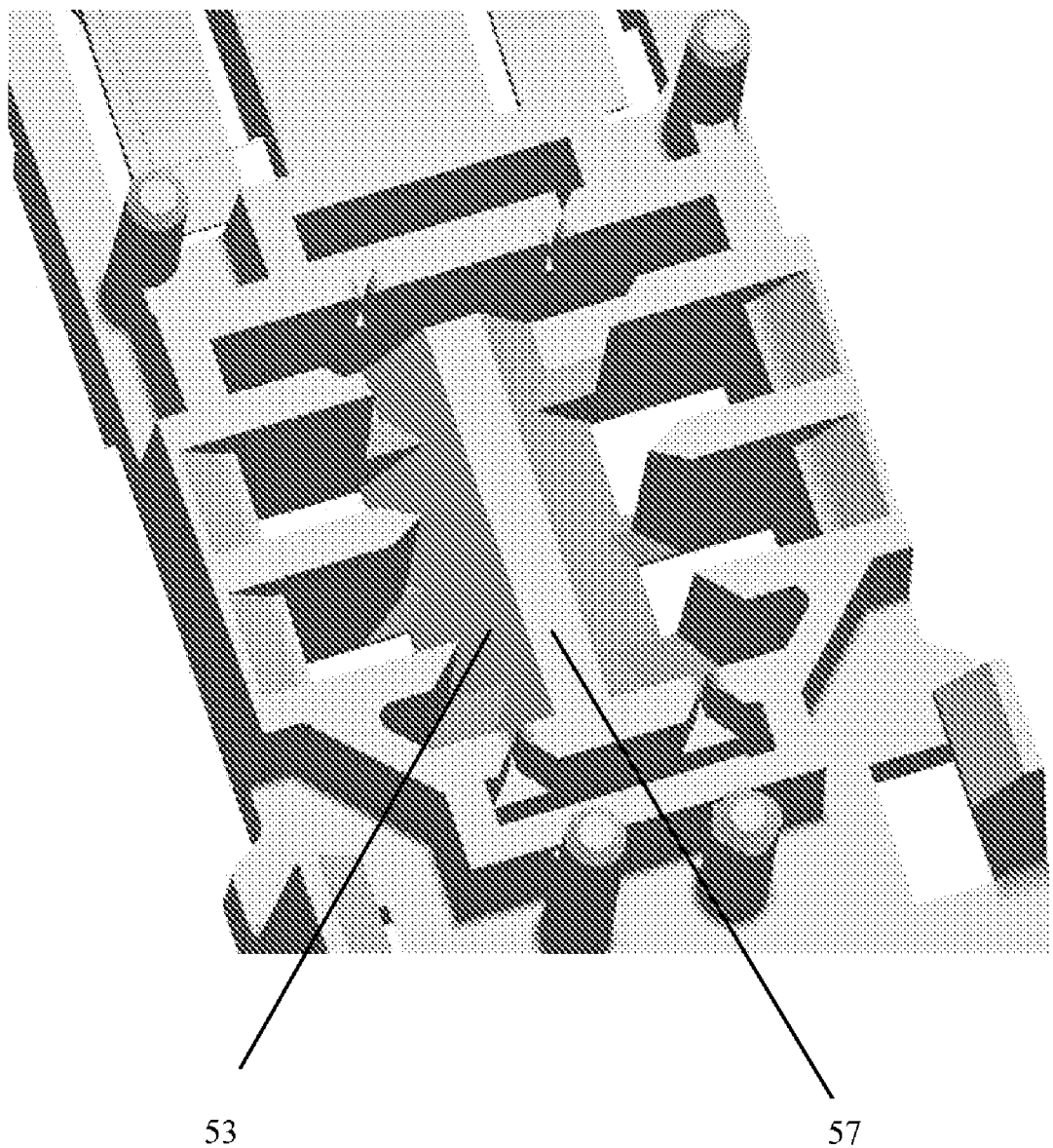

FIG. 5b shows an underside view of the baffle arrangement of the exemplified embodiment from a different perspective. The sloping member (53) is symmetrical about axis (57) and serves to guide reflected light from all four LEDs (not shown) onto the photodetector (not shown).

Figure 6:
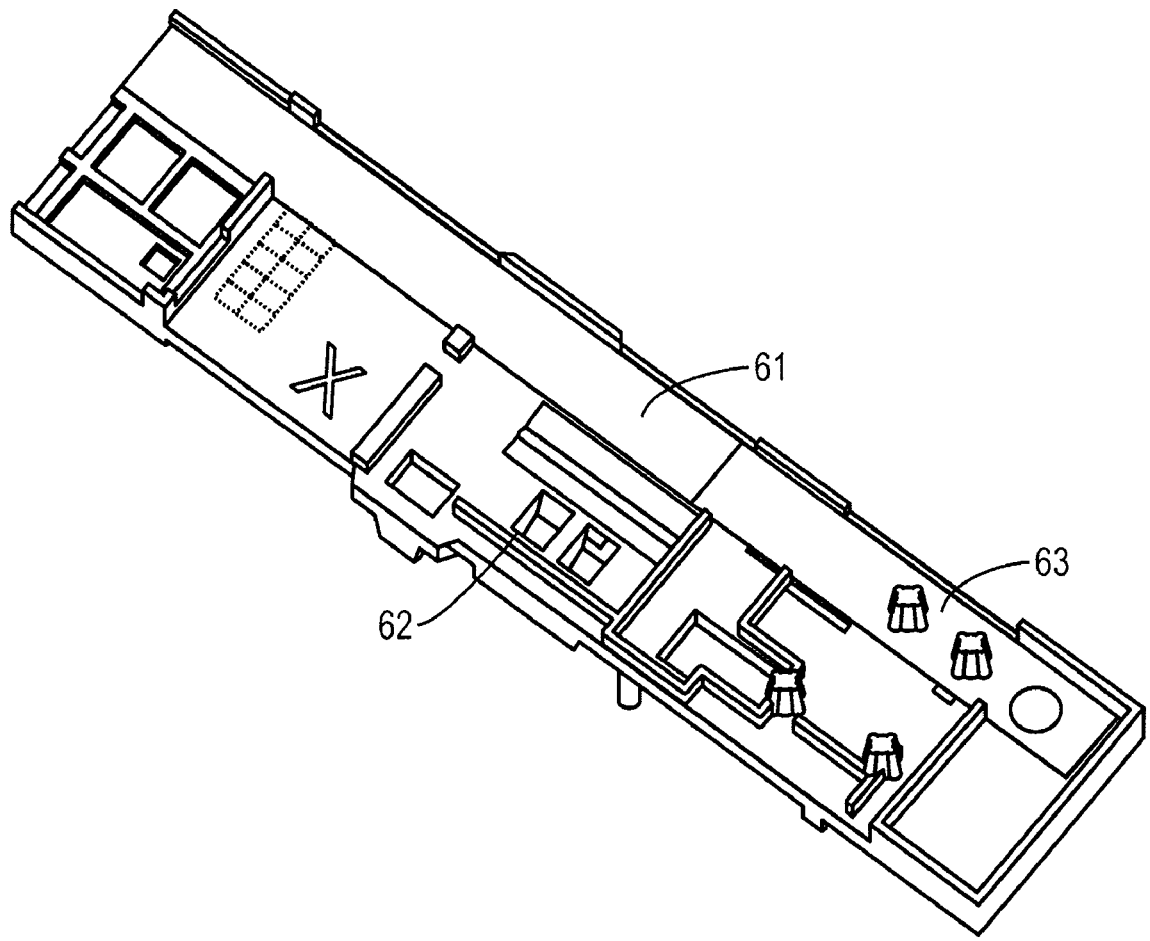
FIG. 6 is a top view of the part of the assay device embodiment depicted in preceding figures, and illustrating a lateral flow test-strip in situ in the assay device.

FIG. 6 shows top view of the assay device looking down onto a test-strip (61) located over the apertures (62) and held in position by locating pins (63). The LEDs and photodetector can be partially seen through the apertures.

Example 1

The value of the signal determined from the respective zones for an assay device comprising a low sensitivity test-zone (for measuring high analyte concentration) and a high sensitivity test-zone (for measuring low analyte concentration) is determined by the signal computation means as follows:

The use of the strips and windows are defined in the table below (see FIG. 2)

| Strip | Window 1 | Window 2 |
| --- | --- | --- |
| A | Low Sensitivity test line (LS) | Control line (Ctrl) |
| B | High Sensitivity test line (HS) | Reference window (Ref) |

Measurements of the light reflected from each window are taken approximately twice a second and a low pass digital filter is used to reject noise and smooth the data. Filtered values are used for detecting flow and determining the result and are expressed in terms of normalised percentage relative attenuation (% A). This takes into account and minimises any variations in the optical components both within the device and between devices.

The measured value is inversely proportional to the quantity of light reflected.

For each window, the window ratio at the reference, control, and test windows is equal to the measured value when the porous carrier is dry, t=0 (prior to addition of sample), divided by the measured value at time t after addition of sample:

Calculation of Filtered Window Ratios

For each time point t the window ratios for each window are evaluated as follows:

$$\text{Ref } ratio_t = \frac{\text{filtered reference window } value_{time=0}}{\text{filtered reference window } value_{time=t}}$$

$$\text{HS } ratio_t = \frac{\text{filtered HS test window } value_{time=0}}{\text{filtered HS test window } value_{time=t}}$$

$$\text{LS } ratio_t = \frac{\text{filtered LS test window } value_{time=0}}{\text{filtered LS test window } value_{time=t}}$$

$$\text{Ctrl } ratio_t = \frac{\text{filtered Ctrl window } value_{time=0}}{\text{filtered Ctrl window } value_{time=t}}$$

Calculation of Filtered % A Values

The normalised percentage relative attenuation (% A) is given by the difference of the reference (ref) window ratio and the window ratio being considered (control or test windows) divided by the reference window ratio and multiplied by 100%.

For each time point t, % A values are calculated for the HS test line, LS test line and control line, wherein:

$$HS_t (\%A) = \frac{\text{Ref } ratio_t - HS \text{ test } ratio_t}{\text{Ref } ratio_t} \times 100\%$$

$$LS_t (\%A) = \frac{\text{Ref } ratio_t - LS \text{ test } ratio_t}{\text{Ref } ratio_t} \times 100\%$$

$$Ctrl_t (\%A) = \frac{\text{Ref } ratio_t - \text{Ctrl } ratio_t}{\text{Ref } ratio_t} \times 100\%$$

Construction of Assay Devices

An assay device according to the first aspect of the invention was constructed comprising a first assay test-strip comprising a labelled binding reagent provided upstream from a detection zone and a second assay test-strip comprising a labelled binding reagent and a second (scavenger) binding reagent for the analyte as well as labelled binding reagent for a control zone provided upstream from a detection zone and a control zone.

Preparation of the First Assay Test-Strip

The detection zone was prepared by dispensing a line of anti-β-hCG antibody (in-house clone 3468) at a concentration of 3 mg/ml in PBSA buffer, at a rate of 1 μl/cm on onto bands of nitrocellulose of dimensions 350 mm length×40 mm width (Whatman) having a pore-size of 8 microns and a thickness between 90-100 microns which had been laminated to a 175 micron backing layer. The anti-β-hCG antibody was applied using the Biodot xyz3050 dispensing platform as a line ~1.2 mm in width and ~300 mm in length at a position of 10 mm along the length of the nitrocellulose.

The bands of nitrocellulose were dried using Hedinair drying oven serial #17494 set at 55° C. and speed 5 (single pass).

The nitrocellulose was subsequently blocked using a blocking buffer comprising a mixture of 5% ethanol (BDH Analar 104766P) plus 150 mM Sodium Chloride (BDH Analar 10241AP) plus 50 mM trizma base from (Sigma T1503) plus Tween 20 (Sigma P1379) and 1% (w/v) polyvinyl alcohol (PVA, Sigma 360627).

The blocking buffer was applied at a rate of 1.75 μl/mm to the proximal end of the band. Once the blocking solution had soaked into the membrane a solution of 2% (w/v) sucrose (Sigma S8501 in deionised water) was applied using the same apparatus at a rate of 1.6 μl/mm and allowed to soak into the nitrocellulose membrane for ~5 minutes).

The bands of NC were then dried using a Hedinair drying oven serial #17494 set at 75° C. and speed 5 (single pass).

Preparation of the Mobilisable Labelled Binding Reagent on the First Porous Carrier Material.

Labelled binding reagent was prepared according to the following protocol:

Coating Latex Particles with Anti-α-hCG

1. Dilute blue latex particles from Duke Scientific (400 nm in diameter, DB1040CB at 10% solids (w/v)) to 2% solids (w/v) with 100 mM di-sodium tetra borate buffer pH 8.5 (BDH AnalaR 102676G) (DTB).
2. Wash the diluted latex by centrifuging a volume of (2 mls) of diluted latex in two Eppendorf centrifuge tubes at 17000 rpm (25,848 rcf) for 10 minutes on an Heraeus Biofuge 17RS centrifuge. Remove and discard the supernatant and re-suspend the pellets in 100 mM DTB to give 4% solids (w/v) in a total volume of 1 ml.
3. Prepare a mixture of ethanol and sodium acetate (95% Ethanol BDH AnalaR 104766P with 5% w/v Sodium Acetate Sigma S-2889).
4. Add 100 μls ethanol-sodium acetate solution to the washed latex in step 2 (this is 10% of the volume of latex).
5. Dilute the stock antibody (in-house clone 3299) to give ~1200 μg/ml antibody in DTB.
6. Heat a volume of 1 ml of the diluted antibody from step 5 in a water bath set at 41.5° C. for ~2 minutes. Also heat the washed latex plus ethanol-sodium acetate from step 4 in the same water bath for 2 minutes.
7. Add the diluted antibody to the latex plus ethanol-acetate, mix well and incubate for 1 hour in the water bath set at 41.5° C. whilst mixing using a magnetic stirrer and a magnetic flea placed in the mixture.
8. Prepare 40 mg/ml Bovine Serum Albumin (BSA) Solution (Intergen W22903 in de-ionised water). Block the latex by adding an equal volume of 40 mg/ml BSA to the mixture of latex/antibody/ethanol-acetate and incubate in the water bath at 41.5° C. for 30 minutes with continued stirring.
9. Centrifuge the mixture at 17000 rpm for 10 minutes as in step 2, (split the volume into 1 ml lots between Eppendorf tubes). Remove and discard the supernatant and re-suspend the pellet in 100 mM DTB. Repeat the centrifugation as in step 2, remove and discard the supernatant and re-suspend in pellet in Air Brushing Buffer (20% (w/v) Sucrose Sigma S8501, 10% BSA (w/v) in 100 mM Trizma Base Sigma T1503 pH to 9). Add Air Brushing Buffer to give 4% solids (w/v) latex.

The conjugated latex was and sprayed in a mixture of BSA and sucrose onto a glass-fibre porous carrier (F529-09, Whatman) at a rate of 50 g/hr and 110 mm/s and dried using a Hedinar Conveyor Oven Serial number 17494 set at 65° C. and speed 5 (single pass).

The zone chosen as the reference zone was at a distance of 13 mm along the nitrocellulose, namely downstream of the detection zone.

The glass fibre material comprising the labelled binding reagent was attached to the nitrocellulose membrane using a clear adhesive coated laminate film (Ferrisgate, 38 mm wide) arranged such that the labelled reagent was uppermost and the glass fibre overlapped the surface of the nitrocellulose by ~2 mm along the length (350 mm) of the band of nitrocellulose membrane. The glass fibre was attached to the end of the nitrocellulose such that it was upstream of the detection zone.

The laminated sheet was subsequently cut into test-strips comprising a glass fibre porous carrier material having a width of 6 mm and a length 25 mm, with the labelled reagents having been applied 20 mm along the length of the glass fibre, provided upstream from and overlapping by 2 mm, a nitrocellulose membrane having a width of 6 mm and a length of 40 mm.

Preparation of the Second Assay Test-Strip.

The detection zone was prepared as follows:

MAb mouse anti-human β-hCG antibody (clone 3468) 3 mg/ml in PBSA buffer was plotted at 1 μl/cm onto nitrocellulose (of type and dimensions as that according to the first assay) at the 10 mm position using a Biodot XYZ3050 dispensing platform to provide a sole detection zone for the first assay.

The control zone was prepared as follows:

Goat-anti-Rabbit antibody (Lampire) at 2 mg/ml in PBSA buffer was plotted at 1 μl/cm onto the same nitrocellulose as used for the second assay, at the 13 mm position using a Biodot XYZ3050 dispensing platform to provide a sole control zone for the assay device.

Mouse-anti-human α-hCG mAb (clone 3299) conjugated to 400 nm blue polystyrene latex (Duke Scientific) was mixed with scavenger antibody mAb mouse anti-human β-hCG (in-house clone 3468) at 3 mg/ml to give a final % blue latex of 3%, a final 3468 concentration of 0.075 mg/ml and 0.06 mg/ml concentration of the free anti-β hCG antibody. The resulting mixture was airbrushed onto Whatman glass fibre (F529 25 mm wide reels) using the BIODOT XYZS (serial number 1673) at 90 g/hr sprayed at 2.02 µg/cm onto F529-09 glass fibre at approximately the 20 mm position. The sprayed solution spread out to form a band that was approximately 7 mm in length.

Labelled binding reagent for the control zone was also deposited onto the same region of the porous carrier as the labelled binding reagent for the analyte as follows:

Rabbit IgG (Dako) was conjugated to 400 nm blue latex polystyrene latex (Duke Scientific) in BSA/sucrose to give a final % blue latex of 0.7% solids and sprayed at 65 g/hr onto glass fibre.

The glass fibre was dried using a Hedinar Conveyor Oven Serial number 17494 set at 65° C. and speed 5 (single pass). A second pass of latex was deposited onto the glass fibre by repeating the above however at an offset of ~0.8 mm from the original position of spray (further downstream of the glass fibre). The glass fibre as dried as described above.

The glass fibre material with sprayed latex was attached to the nitrocellulose membrane using a clear adhesive coated laminate film (Ferrisgate, 38 mm wide) arranged such that the sprayed latex was uppermost and the glass fibre overlapped the surface of the nitrocellulose by approximately 2 mm along the length (350 mm) of the band of nitrocellulose membrane. The glass fibre was provided upstream from the nitrocellulose membrane and the binding reagents were provided towards the distal end of the glass fibre.

The laminated sheet was subsequently cut into test-strips comprising a glass fibre porous carrier material having a width of 6 mm and a length 25 mm, with the labelled reagents having been applied 20 mm along the length of the glass fibre, provided upstream from and overlapping by 2 mm, a nitrocellulose membrane having a width of 6 mm and a length of 40 mm. A porous sample receiver (Filtrona) of 45 mm length, 12 mm width and a thickness of approximately 2.5 mm was provided upstream from and overlapping the first porous carrier material by approximately 3 mm.

Labelled binding reagent for the control zone was also deposited onto the same region of the porous carrier as the labelled binding reagent for the analyte as follows:

Rabbit IgG (Dako) was conjugated to 400 nm blue latex polystyrene latex (Duke Scientific) in BSA/sucrose to give a final % blue latex of 0.7% solids and sprayed at 65 g/hr onto glass fibre (F529-09).

The first and second assay test-strips were positioned parallel to one another and a common polyester sample application pad (505521, Filtrona) was overlaid at the upstream ends of both assays. A common cotton absorbent sink pad (CF7, Whatman) was overlaid downstream of the reference and control zones.

The assay device was prepared by mounting the assay strips in a parallel configuration into a plastic housing comprising the optical components. The LEDs were arranged such that the four LEDs were positioned in close proximity to the respective four zones (2 detection zones and the reference and control zones) in an offset position and above the plane of the assays. A single photodetector was positioned between and above the plane of the two assays and positioned in the middle of the assay strips (see FIG. 2).

EQUIVALENTS

Those skilled in the art will recognize, or be able to ascertain using no more than routine experimentation, many equivalents of the specific embodiments of the invention described herein. Such equivalents are intended to be encompassed by the following claims.

The invention claimed is:

1. An assay device for determining the presence and/or extent of one or more analyses in a liquid sample comprising:
   a) a first and second test strips each comprising a flow-path, and each having a detection zone for immobilizing a labeled binding reagent, wherein detection of a labeled binding reagent at one or both detection zones is indicative of the presence and/or extent of one or more analytes;
   b) a common sample application zone which fluidically connects the first and second test strips;
   c) a shared reference zone;
   d) one or more light sources to illuminate the detection zones and the reference zone;
   e) one or more photodetectors to detect light from the detection zones and the reference zone, which photodetector generates a signal, the magnitude of which signal is related to the amount of light detected; and
   f) signal processing means for processing signals from the photodetector.

2. The assay device according to claim 1, wherein the first and second test strips comprises a labeled binding reagent for an analyte or analyte analogue provided in a mobilizable form upstream from the detection zone in a dry state prior to use of the device.

3. The assay device according to claim 1, wherein the first and/or second test strip comprises a binding reagent for an analyte or a labeled binding reagent provided in an immobilized form at the detection zone.

4. The assay device according to claim 1, further comprising a shared control zone.

5. The assay device according to claim 1, wherein the shared reference zone is comprised as part of either the first or second test strip.

6. The assay device according to claim 4, wherein the control zone is comprised as part of either the first or second test strip.

7. The assay device according to claim 4, wherein the control zone is comprised as part of one and the shared reference zone is comprised as part of the other test strip.

8. The assay device according to claim 1, wherein the first test strip and second test strip are capable of detecting the presence of an analyte in different concentration ranges.

9. The assay device according to claim 1, wherein the flow-paths of the first and second test strips each comprise a porous carriers.

10. The assay device according to claim 9, wherein the porous carrier comprises nitrocellulose.

11. The assay device according to claim 1, comprising a single porous sample receiver provided upstream from the first and second test strips.

12. The assay device according to claim 1, further comprising a sink provided at the distal end of the test strip flow-paths.

13. The assay device according to claim 1, wherein the first and second test strips each comprise different amounts of labeled binding reagent.

14. The assay device according to claim 1, comprising a first test strip for the detection of an analyte in a lower range and a second test strip for the detection of analyte in a higher range.

15. The assay device according to claim 14 wherein the second test strip has a greater amount of labeled binding reagent than the first test strip.

16. The assay device according to claim 1, wherein the first test strip comprises a labeled binding reagent for the analyte provided upstream from a detection zone and the second test strip comprises a labeled binding reagent for the analyte and a second binding reagent for the analyte provided upstream from the detection zone.

17. The assay device according to claim 16, wherein the first test strip comprises a shared reference zone and the second test strip comprises a shared control zone.

18. The assay device according to claim 17, wherein the reference zone is provided downstream from the detection zone.

19. The assay device according to claim 17, wherein the control zone is provided downstream from the detection zone.

20. The assay device according to claim 1, wherein a photodetector detects light from a plurality of zones.

21. The assay device according to claim 20, comprising a single photodetector to detect light from the two detection zones, the reference zone and the control zone.

22. The assay device according to claim 21, comprising four light sources to illuminate the two detection zones, the reference zone and the control zone.

23. The assay device according to claim 20, wherein the amount of light detected by the photodetector from the detection zones and the reference zone is measured prior to addition of sample to the assay device and again after addition of sample to the assay device, and a ratio of the two measurements calculated for each zone.

24. The assay device according to claim 20, wherein a normalised percentage relative attenuation (% A) is calculated for the detection and/or control zones wherein:

$$HS_t\,(\%A) = \frac{\text{Ref }ratio_t - HS\text{ test }ratio_t}{\text{Ref }ratio_t} \times 100\%$$

$$LS_t\,(\%A) = \frac{\text{Ref }ratio_t - LS\text{ test }ratio_t}{\text{Ref }ratio_t} \times 100\%$$

$$Ctrl_t\,(\%A) = \frac{\text{Ref }ratio_t - \text{Ctrl }ratio_t}{\text{Ref }ratio_t} \times 100\%.$$

25. The assay device according to claim 1, wherein the light source comprises one or more LEDs.

26. The assay device according to claim 1, wherein the analyte to be determined is hCG.

27. The assay device according to claim 1, wherein the liquid sample is urine.

* * * * *